(12) United States Patent
Boyette et al.

(10) Patent No.: US 8,481,302 B2
(45) Date of Patent: Jul. 9, 2013

(54) TOTAL BACTERIA MONITORING SYSTEM

(75) Inventors: Scott M. Boyette, New Hope, PA (US); Hong Cai, Shanghai (CN); Yan Jin, Shanghai (CN); Jie Li, Shanghai (CN); Kechao Yang, Shanghai (CN); Rong Xu, Shanghai (CN); Yu Wang, Shanghai (CN)

(73) Assignee: General Electric Company, Schenectady, NY (US)

( * ) Notice: Subject to any disclaimer, the term of this patent is extended or adjusted under 35 U.S.C. 154(b) by 378 days.

(21) Appl. No.: 12/472,024

(22) Filed: May 26, 2009

(65) Prior Publication Data

US 2010/0112682 A1 May 6, 2010

Related U.S. Application Data

(63) Continuation-in-part of application No. 12/263,829, filed on Nov. 3, 2008.

(51) Int. Cl.
*C12M 1/00* (2006.01)
*C12M 1/36* (2006.01)
*C12M 1/38* (2006.01)
*C12M 3/00* (2006.01)
*C12M 1/34* (2006.01)

(52) U.S. Cl.
USPC ............... 435/288.7; 435/283.1; 435/287.1; 435/289.1; 435/286.4; 435/286.2

(58) Field of Classification Search
USPC .................................. 435/288.7, 283.1–309.4
See application file for complete search history.

(56) References Cited

U.S. PATENT DOCUMENTS

| 3,864,212 A | 2/1975 | Berkhan |
| 4,225,669 A | 9/1980 | Melnick |
| 4,242,447 A | 12/1980 | Findl |
| 4,385,113 A | 5/1983 | Frosch |
| 4,544,546 A | 10/1985 | Wang |

(Continued)

FOREIGN PATENT DOCUMENTS

| CN | 1876829 A | 12/2006 |
| EP | 0168933 A2 | 1/1986 |
| EP | 1329514 A2 | 7/2003 |
| WO | 2005/056689 A2 | 6/2005 |

OTHER PUBLICATIONS

Dexter S J et al: "Development of a bioluminescent ATP assay to quantify mammalian and bacterial cell number from a mixed population", Biomatertals, Jan. 1, 2003, pp. 27-34. vol. 24, Iss 1, Elsevier Science Pubitshers BV, Barking; GB.

(Continued)

*Primary Examiner* — William H Beisner
*Assistant Examiner* — Lydia Edwards
(74) *Attorney, Agent, or Firm* — Wegman, Hessler & Vanderburg

(57) ABSTRACT

A system for measuring total microbiological content in an aqueous medium by adding a fluorescent dye to the aqueous medium, measuring the fluorescent signal in the aqueous medium to obtain a baseline fluorescent signal, releasing intracellular content of the microbiological matter into the aqueous medium by lysing the microbiological matter. The system then measures the fluorescent signal in the aqueous medium with the released intracellular content of the microbiological matter to obtain a second fluorescent signal. Next, the system subtracts the baseline signal from the second fluorescent signal to obtain a net fluorescent signal and equates the net fluorescent signal with a microbiological content.

22 Claims, 5 Drawing Sheets

U.S. PATENT DOCUMENTS

| | | | |
|---|---|---|---|
| 4,591,554 A | | 5/1986 | Koumura |
| 4,639,421 A | | 1/1987 | Sage, Jr. |
| 4,693,972 A | | 9/1987 | Mansour et al. |
| 4,698,308 A | | 10/1987 | Ikeda |
| 5,049,492 A | | 9/1991 | Sauer et al. |
| 5,164,301 A | | 11/1992 | Thompson |
| 5,292,644 A | | 3/1994 | Berg |
| 5,349,874 A | | 9/1994 | Schapira et al. |
| 5,443,987 A | | 8/1995 | Decicco |
| 5,464,773 A | | 11/1995 | Melendez et al. |
| 5,487,981 A | | 1/1996 | Nivens et al. |
| 5,488,856 A | | 2/1996 | Dirk |
| 5,498,525 A | | 3/1996 | Rees |
| 5,510,246 A | | 4/1996 | Morgan |
| 5,545,535 A | | 8/1996 | Roth |
| 5,605,812 A | | 2/1997 | Zomer |
| 5,643,767 A | | 7/1997 | Frischetti et al. |
| 5,677,140 A | | 10/1997 | Denzler |
| 5,809,185 A | | 9/1998 | Mitchell |
| 5,812,419 A | * | 9/1998 | Chupp et al. ............... 702/20 |
| 5,891,394 A | | 4/1999 | Drocourt |
| 5,968,762 A | | 10/1999 | Jadamec |
| 6,250,140 B1 | | 6/2001 | Kouznetsov et al. |
| 6,326,190 B1 | | 12/2001 | Ceri et al. |
| 6,329,165 B1 | | 12/2001 | Chattoraj et al. |
| 6,395,504 B1 | | 5/2002 | Trudil |
| 6,405,582 B1 | | 6/2002 | Boettcher |
| 6,498,862 B1 | | 12/2002 | Pierson et al. |
| 6,569,627 B2 | | 5/2003 | Witter et al. |
| 6,599,714 B1 | | 7/2003 | Ceri et al. |
| 6,623,945 B1 | | 9/2003 | Nair et al. |
| 6,660,472 B1 | | 12/2003 | Santoro et al. |
| 6,699,684 B2 | | 3/2004 | Ho et al. |
| 6,777,226 B2 | | 8/2004 | Jeffrey |
| 6,844,157 B2 | | 1/2005 | Snaidr |
| 6,942,169 B2 | | 9/2005 | Sparks |
| 7,143,640 B2 | | 12/2006 | Daley |
| 7,190,457 B2 | | 3/2007 | Tabacco et al. |
| 2003/0228599 A1 | * | 12/2003 | Straus ............... 435/6 |
| 2004/0009473 A1 | | 1/2004 | Pease |
| 2004/0229368 A1 | * | 11/2004 | Rubio et al. ............... 436/63 |
| 2005/0042661 A1 | | 2/2005 | Tarkkanen et al. |
| 2006/0078475 A1 | * | 4/2006 | Tai et al. ............... 422/102 |
| 2006/0115902 A1 | | 6/2006 | Han et al. |
| 2006/0166307 A1 | | 7/2006 | Detraz et al. |
| 2007/0178514 A1 | * | 8/2007 | van Beuningen ............... 435/6 |
| 2007/0196884 A1 | * | 8/2007 | Bodini et al. ............... 435/18 |

OTHER PUBLICATIONS

International Search Report issued in connection with corresponding PCT Application No. PCT/US2009/059239 on Mar. 5, 2010.

Written Opinion issued in connection with corresponding PCT Application No. PCT/US2009/059239 on Mar. 5, 2010.

A Proteomic Strategy for the Identification if Caspase-Associating Proteins, Eunice L.P. Tan et al., Chem. Commun., 2004, pp. 596-598.

Accurate Flow Cytometric Membrane Potential Measurement in Bacteria Using Diethyloxacarbocyanine and a Ratiometric Technique, David Novo et al. Department of Medicine, McMaster University, Hamilton, Ontario, Canada 1998.

Activity-Based High-Throughput Screening of Enzymes by Using a DNA Microarray, Yi Hu et al., Angewandte Chemie International, 2004 Abstract.

Activity-Based Probes for the Proteomic Profiling of Metalloproteases, Alan Saghatelian et al., The Skaggs Institute for Chemical Biology and Departments of Cell Biology and Chemistry, The Scripps Research Institute, Jun. 25, 2004.

Antimicrobial Peptides: Pore Formers or Metabolic Inhibitors in Bacteria, Kim A. Brogden, Nature Reviews Microbiology 3., pp. Mar. 2005 Abstract.

Comparison of Propidium Monoazide With Ethidium Monoazide for Differentiation of Live vs Dead Bacteria by Selective Removal of DNA From Dead Cells, Andreas Nocker et al., Journal of Microbiological Methods, vol. 67, Issuse 2, Nov. 2006, pp. 310-320 Abstract.

Comparison of Rapid Methods for the Extraction of Bacterial DNA From Colonic and Caecal Lumen Contents of the Pig, K.L. Anderson et al., USDA/ARS, National Swine Research and Information Center, Ames IA USA, Journal of Applied Microbiology, 2003, 94, pp. 988-993.

Continuous Flow Microfluidic Device for Rapid Erythrocyte Lysis, Palaniappan Sethu et al., Anal. Chem vol. 76, 2004 pp. 6247-6253.

Detection of mRNA by Reverse Transcription-PCR as an Indicator of Viability in *Escherichia coli* Cells, G.E.C. Sheridan et al., Institute of Food Research, Reading, UK, Applied and Environmental Microbiology, Apr. 1998, pp. 1313-1318.

Developing Novel Activity-Based Fluorescent Probes that Target Different Classes of Proteases, Qing Zhu, et al., The Royal Society of Chemistry 2004 pp. 1512-1513.

Effects of Shear Stress on Endothelial Cells: Possible Relevance for Ultrasound Applications, E. VanBavel, Progress in Biophysics and Molecular Biology 2007, vol. 93, pp. 374-383.

Enumeration and Characterization of Standard Plate Count Bacteria in Chlorinated and Raw Water Supplies, Mark W. LeChevallier et al., Department of Microbiology, Oregon State University, Oregon, Applied and Environmental Microbiology, vol. 40. No. 5, Nov. 1980, pp. 922-930.

Enumeration of Bacterial Cell Numbers by Amplified Firefly Bioluminescence Without Cultivation, Tatsuya Sakakibara et al., Analytical Biochemistry vol. 312, 2003 pp. 48-56.

Estimation of Membrane Potentials of Individuals Lymphocytes by Flow Cytometry, Howard M. Shapiro et al., Proc. Natl. Acad. Sci. USA, vol. 76, No. 11, pp. 5728-5730 Nov. 1979.

Bacterial Chromosome Extraction and Isolation Lab Chip, Christelle Prinz, et al. vol. 2, 2002 pp. 207-212.

Flourescence Detection of ATP based on the ATP-Mediated Aggregation of Pyrene-Appended Boronic Acid on a Polycation, Yasumasa Kanekiyo et al., National Institute of Advanced Industrial Science and Technology, Japan Chem, Commun., 2004, 1006-1007.

Flourogenic and Chromogenic Substrates Used in Bacterial Diagnostics, Mohammed Manafi et al., Microbiological Reviews, Sep. 1991, p. 335-348.

The Future Challenges Facing the Development of New Antimicrobial Drugs, Anthony Coates et al., Nature Reviews, Drug Discovery vol. 1, Nov. 2002 p. 895-910.

A High-Throughput Screening Assay for Kinases and Phosphatases via Metal Ion-Mediated Flourescent Polymer Superquendhing, Wensheng Xia et al., American Laboratory Oct. 2004, p. 15-19.

Initial Investigations into the Ultrasonic Lysis of Microbial Cells for the Release of Adenosine Triphosphate, Karen A Law et al., Analytical Biochemistry vol. 317, 2003 p. 226-267.

Investigations of DNA Intercalation and Surface Binding by SYBR Green I, its Structure Determination and Methodological Implications, Hubert Zipper et al., Nucleic Acids Research, 2004, vol. 32 No. 12.

Lysing Bacterial Spores by Sonication Through a Flexible Interface in a Microfluidic System, Michael T. Taylor et al., Anal. Chem 2001, vol. 73, p. 492-496.

Microarray Platform for Profiling Enzyme Activities in Complex Proteomes, Stephen A. Sieber et al., Journal of the American Chemical Society 2004 Abstract.

Multiparameter Flow Cytometric Analysis of Antibiotic Effects on Membrane Potential, Membrane Permeability, and Bacterial Counts of *Staphylococcus aureus* and *Micrococcus luteus*, David Novo, et al., Antimicrobial Agents and Chemotherapy Apr. 2000, vol. 44, No. 4, p. 827-834.

Multiparameter Flow Cytometry of Bacteria: Implications for Diagnostics and Therapeutics, Howard Shapiro MD, Cytometry vol. 43, 2001, p. 223-226.

A New Procedure for Efficient Recovery of DNA, RNA, and Proteins From *Listeria* Cells by Rapid Lysis with a Recombinant Bacteriophage Endolysin, Martin Loessner et al., Applied and Environmental Microbiology, Mar. 1995 vol. 61, No. 3 p. 1150-1152.

Polymerase Chain Reaction-Gene Probe Detection of Microorganisms by Using Filter-Concentrated Samples Asim K Bej et al., Applied and Environmental Microbiology, Dec. 1991 vol. 57, No. 12 p. 3529-3534.

Preparation and Hybridization Analysis of DNA/RNA from *E. coli* on Microfabricated Bioelectronic Chips, Jing Cheng et al., Nature Biotechnology vol. 16, Jun. 1998, p. 541-546.

Rapid Fluorescence Assessment of the Viability of Stressed *Lactococcs lactis*, Christine J. Bunthof et al., Applied and Environmental Microbiology Aug. 1999 vol. 65, No. 8 p. 3681-3689.

Rapid Method of Detection of Gram-Positive and -Negative Bacteria in Milk from Cows with Moderate or Severe Clinical Mastitis, Siamak P. Yazdankhah et al., Journal of Clinical Microbiology, Sep. 2001, vol. 39 No. 9, p. 3228-3233.

Reagentless Mechanical Cell Lysis by Nanoscale Barbs in Microchannels for Sample Preparation, Dino DiCarlo et al., Lab Chip, vol. 3, 2003 p. 287-291.

A Real-Time DNase Assay (ReDA) Based on PicoGreen Fluorescence, Gokhan Tolun et al., Nucleic Acids Research, 2003, vol. 31, No. 18.

Selective Removal of DNA from Dead Cells of Mixed Bacterial Communities by Use of Ethidium Monoazide, Andreas Nocker et al., Applied and Environmental Microbiology, Mar. 2006, vol. 72, No. 3 p. 1997-2004.

Single-Cell Chemical Lysis in Picoliter-Scale Closed Volumes Using a Microfabricated Device, Daniel Irimia et al., Analytical Chemistry, Oct. 2004, vol. 76, No. 20 p. 6137-6143.

Use of Heat Release and an Internal RNA Standard Control in Reverse Transcription-PCR Detection of Norwalk Virus from Stool Samples, K.J. Schwab, et al., Journal of Clinical Microbiology, Feb. 1997, vol. 35, No. 2 p. 511-514.

Use of *Toxoplasms gondii* Expressing B-Galactosidase for Colorimetric Assessment of Drug Activity in Vitro, Diane C. McFadden et al., Antimicrobial Agents and Chemotherapy, Sep. 1997, vol. 41, No. 9, p. 1849-1853i.

Antibiotic Resistance of Bacteria in Biofilms, P. Stewart et al., Lancet 2001; vol. 358 p. 135-138.

National Institutes of Health Guide for Grant Applications for Research on Microbial Biofilms Dec. 20, 2002.

Influence of Fouling Biofilms on Heat Transfer, W.G. Characklis et al., Heat Transfer Engineering, vol. 3, No. 1, Jul.-Sep. 1981.

*Pseudomonas* biofilm formation and antibiotic resistance are linked to phenotypic variation, Eliana Drenkard et al., Nature, vol. 416, Apr. 18, 2002.

Biofilm Growth and Detachment of *Actinobacillus actinomycetemcomitans*, Jeffrey B. Kaplan et al., Journal of Bacteriology, Feb. 2003 vol. 185, No. 4 p. 1399-1404.

Biofilm Formation by the Fungal Pathogen *Candida albicans*: Development, Architecture, and Drug Resistance, Jyotsna Chandra et al., Journal of Bacteriology, Sep. 2001, vol. 183, No. 18 p. 5385-5394.

Particle-Based Multidimensional Multispecies Biofilm Model, Christian Picioreanu et at., Applied and Environmental Microbiology, May 2004, vol. 70, No. 5, p. 3024-3040.

Electric Current-Induced Detachment of *Staphylococcus epidermis* Biofilms from Surgical Stainless Steel, Arnout J. van der Borden et al., Applied and Environmental Microbiology Nov. 2004 vol. 70, No. 11 p. 6871-6874.

Removal and Inactivation of *Staphylococcus epidermis* Biofilms by Electrolysis, Christine Rabinovitch et al., Applied and Environmental Microbiology Sep. 2006 vol. 72, No. 9 p. 6364-6366.

* cited by examiner

TOTAL BACTERIA MONITORING SYSTEM

CROSS REFERENCE TO RELATED APPLICATION

This application is a Continuation-In-Part of and incorporates by reference U.S. application Ser. No. 12/263,829 entitled "METHODS FOR MEASURING MICROBIOLOGICAL CONTENT IN AQUEOUS MEDIA" filed Nov. 3, 2008.

BACKGROUND OF THE INVENTION

1. Field of Invention

The present invention relates to systems for quantifying microbiological content in aqueous media and more particularly, to fluorescence-based assays for measuring total microbiological content.

2. Description of Related Art

The presence of microbial activity in public and industrial water systems can cause health risks. Furthermore, detection and control of microorganisms in industrial systems is critical to various businesses, because the presence of such organisms contributes significantly to system corrosion, deposition and fouling and directly impacts the operation costs of the systems. Monitoring microbial concentrations in industrial systems and public water systems, and treatment of these systems, such as by the application of biocides, is an important part of maintaining these systems.

Conventional monitoring systems for microbial detection use culture-based methods or biochemluminescence-based methods. Both of these methods quantify microbial population; however, there are intrinsic shortcomings and defects affiliated with both of these methods. The culture-based method requires lengthy incubation time and often underestimates the microbial numbers due to the composition of the incubation medium. The biochemluminescence method is fast, but has poor accuracy and false positive and false negative results are frequently obtained.

Biofilms present additional concerns for monitoring microbial concentrations. Biofilms are groups of microbes that grow in complex aggregations and adhere to inert or living surfaces. Cells in a biofilm are held tightly to each other by a matrix of polymeric compounds, such as exopolysaccharides, lipopolysaccharides or glycoproteins. In addition to the fouling, corrosion problems, and health concerns noted above, biofilms can reduce heat transfer and hydraulic pressure in industrial cooling water systems, plug water injection jets and clog water filters, and result in microbial influenced corrosion. Biofilms are protected by layers of expolymers and are extremely resistant to disinfectants and other biocides.

What is needed is an accurate and rapid system and method having a high degree of sensitivity for quantifying microbiological content, including quantifying biofilm content, in aqueous media.

SUMMARY OF THE INVENTION

A system has been found that measures the total microbiological content in an aqueous medium by adding a fluorescent dye to the aqueous medium, measuring the fluorescent signal in the aqueous medium to obtain a baseline fluorescent signal, and then releasing intracellular content of the microbiological matter into the aqueous medium by lysing the microbiological matter. The system then measures the fluorescent signal in the aqueous medium with the released intracellular content of the microbiological matter to obtain a second fluorescent signal. Next, the system subtracts the baseline signal from the second fluorescent signal to obtain a net fluorescent signal and equates the net fluorescent signal with a microbiological content.

In another embodiment, the total microbiological content system includes a sample preparation module configured to add a fluorescent dye to the aqueous medium and a lysing module for releasing intracellular content of microbiological matter into the aqueous medium. The system also includes a detection module that has an optical measurement unit that measures the fluorescent signal in the aqueous medium to obtain a baseline fluorescent signal and then measures the fluorescent signal in the aqueous medium with the released intracellular content of the microbiological matter to obtain a second fluorescent signal. The system also contains a control module that subtracts the baseline signal from the second fluorescent signal to obtain a net fluorescent signal and equates the net fluorescent signal with a microbiological content of the aqueous medium.

The various embodiments provide improved systems for measuring total microbiological content in aqueous media, which are easy to use, inexpensive and accurate with a high degree of sensitivity and can be completed in a short period of time.

DETAILED DESCRIPTION OF THE INVENTION

Figure 1:
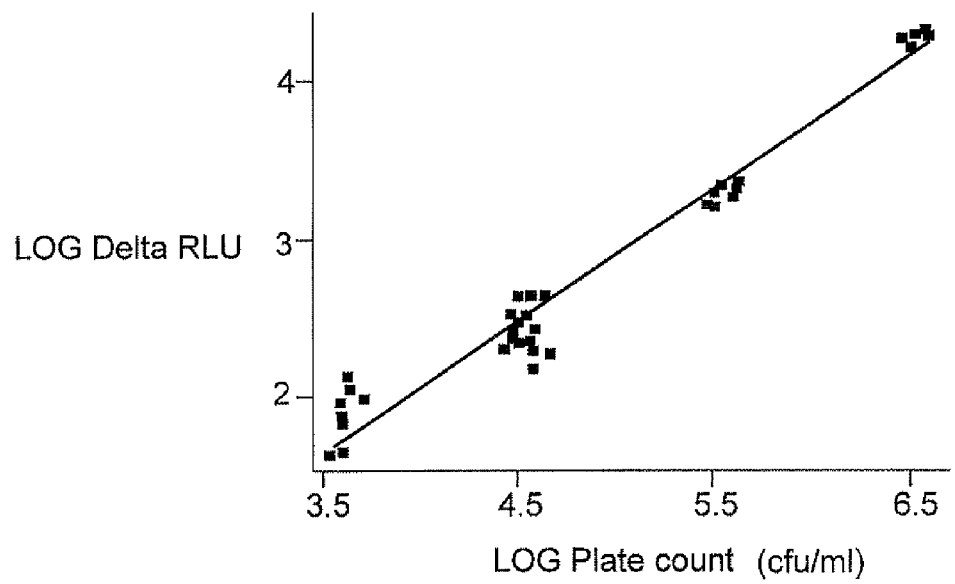
FIG. 1 depicts a graph of a regression plot of LOG delta RLU versus LOG cell concentration (cfu/ml) for *Pseudomonas fluorescens* diluted in autoclaved phosphate buffer saline (PBS).

The singular forms "a," "an" and "the" include plural referents unless the context clearly dictates otherwise. The endpoints of all ranges reciting the same characteristic are independently combinable and inclusive of the recited endpoint. All references are incorporated herein by reference.

The modifier "about" used in connection with a quantity is inclusive of the stated value and has the meaning dictated by the context (e.g., includes the tolerance ranges associated with measurement of the particular quantity).

"Optional" or "optionally" means that the subsequently described event or circumstance may or may not occur, or that the subsequently identified material may or may not be present, and that the description includes instances where the event or circumstance occurs or where the material is present, and instances where the event or circumstance does not occur or the material is not present.

In one embodiment, a process for measuring total microbiological content in an aqueous medium including adding a fluorescent dye to the aqueous medium, measuring the fluorescent signal in the aqueous medium to obtain a baseline fluorescent signal, releasing intracellular content of the microbiological matter into the aqueous medium by lysing the microbiological matter, measuring the fluorescent signal in the aqueous medium with the released intracellular content of the microbiological matter to obtain a second fluorescent signal, subtracting the baseline signal from the second fluorescent signal to obtain a net fluorescent signal and equating the net fluorescent signal with a microbiological content.

The process measures total microbiological content in an aqueous medium. The microbiological matter may be microbes, such as bacteria. Non-limiting examples of bacteria include *Pseudomonas aeruginosa, Pseudomonas fluorescens, Pseudomonas putida, Desulfovibrio desulfuricans, Klebsiella, Comamonas terrigena, Nitrosomonas europaea, Nitrobacter vulgaris, Sphaerotilus natans, Gallionella species, Mycobacterium terrae, Bacillus subtilis, Flavobacterium breve, Salmonella enterica, enterica serovar Typhimurium, Bacillus atrophaeus* spore, *Bacillus megaterium, Enterobacter aerogenes, Actinobacillus actinomycetemcomitans, Candida albicans* and *Ecsherichia coli.*

Aqueous medium may be any type of aqueous media that may contain microbiological matter including aqueous media into which biofilm microbes have been dislodged or dispersed. In one embodiment, the aqueous medium is water. In one embodiment, the water may be municipal water or industrial water, such as cooling tower water. In another embodiment, the aqueous medium may be aqueous solutions for personal care product manufacturing or food and beverage or pharmaceutical processing. In one embodiment, the aqueous media may be a saline solution. In another embodiment, the aqueous media may be a phosphate buffer solution.

A fluorescent dye is added to the aqueous medium. The fluorescent dye may be any type of dye that changes its fluorescence signal in the presence of microbiological matter. In one embodiment, the fluorescent dye is a fluorochrome, which is a microbiological staining dye that binds with biological cellular components, such as nucleic acids, proteins, cytoplasmic components and membrane components.

Examples of fluorochromes include, but are not limited to, acridine orange, ethidium bromide, Hoechst 33258, Hoechst 33342, propidium iodide, 4',6-diamidino-2-phenylindole and nucleic acid dyes available commercially, such as PicoGreen®, SYTO® 16, SYBR® Green I, SYBR® Green II, SYBR® Gold, YOYO™ TOTO™, TO-PRO®, YO-PRO®, Texas Red®, Redmond Red®, Bodipy® Dyes or Oregon Green®. Fluorochromes are commercially available from Molecular Probes (Eugene, Oreg.), Sigma Chemical (St Louis, Mo.), Amersham (Arlington Heights, Ill.), Callbiochem-Novabiochem (La Jolla, Calif.) or Synthetic Genetics (San Diego, Calif.). In another embodiment, the fluorochrome dye may be a cyanine dye, which is available commercially as PicoGreen®, TOTO™, SYBR® Green I, SYBR® Green II, SYBR® Gold or SYBR® Green I. In another embodiment, fluorochrome dye is an asymmetrical cyanine dye, such as SYBR® Green I.

The fluorescent dye is added to the aqueous medium in an amount suitable for fluorescing the microbiological matter in the aqueous medium. In one embodiment, the fluorescent dye is added in an amount of from about 0.5 mg to about 100 mg fluorescent dye per liter of aqueous medium. In another embodiment, the fluorescent dye is added in an amount of from about 0.5 mg to about 10 mg per liter of aqueous medium. In another embodiment, the dye is added in an amount of from about 0.5 mg to about 1.0 mg per liter of aqueous medium.

In one embodiment, a portion of the aqueous medium is removed for testing. Portions of the aqueous medium may be removed manually or may be removed systematically by an online testing device. The fluorescent dye is added to the aqueous medium and dispersed by mixing. In another embodiment, a solution of the fluorescent dye is injected into the aqueous medium sample and blended.

When using a fluorochrome, the pH of the aqueous medium is maintained within a suitable range for optimizing the fluorescence of the dye. In one embodiment, the pH of the aqueous medium is maintained from about 4.0 to about 9.5. In another embodiment, the pH of the aqueous medium is maintained from about 7.0 to about 8.0.

In one embodiment, a buffer is added to the aqueous medium to maintain the pH of the aqueous medium within a suitable range. The buffer may be any type of buffer that does not affect the microbiological matter or fluorescence measurements in the aqueous medium. In one embodiment, the buffer is an inorganic buffer, such as phosphate buffered saline or borate buffer. In another embodiment, the buffer is an organic buffer, such as tris(hydroxymethyl)aminomethane, ethylenediaminetetraacetic acid, N-2-hydroxyethylpiperazine-N'-2-ethanesulfonic acid or mixtures thereof. In one embodiment, the buffer is a blend of tris(hydroxymethyl)aminomethane and ethylenediaminetetraacetic acid. In another embodiment, a blend of tris(hydroxymethyl)aminomethane in a concentration range of about 1 mol/L to about 30 mmol/L and ethylenediaminetetraacetic acid in a concentration range of about 100 mmol/L to about 3 mmol/L is in a molar ratio of about 10:1.

The buffer may be added before or after the fluorochrome is added to the aqueous medium. In one embodiment, the fluorochrome and buffer are premixed and added together to the aqueous medium.

In one embodiment, the buffer is added to the aqueous medium in an amount of from about 1 percent by volume to about 30 percent by volume based on the volume of the aqueous medium. In another embodiment, the buffer is added to the aqueous medium in an amount of from about 1 percent by volume to about 15 percent by volume based on the volume of the aqueous medium. In another embodiment, the buffer is added to the aqueous medium in an amount of from about 5 percent by volume to about 10 percent by volume based on the volume of the aqueous medium.

A baseline fluorescent signal is obtained by measuring the fluorescence of the aqueous medium with the fluorescent dye. As used herein, "fluorescent" means the light emitted by a compound when excited by a shorter wavelength light. The excitation and emission wavelengths depend on the fluorescent dye selected. In one embodiment, the excitation wavelength is from about 350 nm to about 600 nm and the emission wavelength is from about 450 nm to about 650 nm.

Fluorescence may be measured by any type of fluorescence detector. In one embodiment, the fluorescent signal is measured by fluorescence spectroscopy, fluorescence microscopy, fluorescence diode array detection, micro plate fluorescence reading or fluorescence-based flow cytometry. In one embodiment, the fluorescence detector is a portable fluorescence-based detection device or an online water condition monitoring instrument having fluorescence spectroscopy. In one embodiment, the portable fluorescence-based detection device has an LED excitation light and a PMT emission detector. In one embodiment, the portable fluorescence-based detection device has an LED excitation light and a photodiode emission detector.

The measurement is performed rapidly and several measurements may be taken and averaged. Microbiological matter may be detected at a concentration as low as $10^4$ colony forming units (cfu) per milliliter of aqueous medium tested without requiring a pre-test concentration process.

The baseline measurement can be recorded manually or is measured and stored in an online monitoring instrument.

The fluorescent dye stains microbiological cellular components, but cannot permeate in-tact cell membranes of the microbiological cells. To measure total microbiological content, the intracellular content of the microbiological matter is released into the aqueous medium where it can be contacted by the fluorescent dye. In one embodiment, the intracellular contents of microbiological matter is released by lysing cells of the microbiological matter, which breaks apart the cell membrane. Lysing may be performed using mechanical, chemical, physical, electrical, ultrasonic or microwave methods or any combination of these methods.

Mechanical lysing physically disrupts the cell barriers, such as by shear, vibration or force. Examples of mechanical methods include, but are not limited to, pressure-driven cell flow through filter-like structures or small scale bars in fluidic channels, osmotically stressing cells with rapid diffusional mixing of low ionic-strength water, subjecting cells to shear forces while entering a special region with sharp small-scale structures, disrupting cell barriers with a minibead beater or bead mill or applying ultrasonic energy to the cells in the aqueous medium.

Chemical lysing occurs when chemicals are used to disrupt the cell barriers and allow the intracellular content to be released. Any chemical may be used that can disrupt the cell barriers. In one embodiment, detergents, enzymes, extraction solvents or lysing buffers are used. Detergents include, but are not limited to, dodecyl sulfate, 3-[(3-cholamidopropyl)dimethylammonio]-1-propane sulfonate, TWEEN™ 20 detergent, TRITON™ X series detergents, sodium cholate, sodium deoxycholate, guanidinium chloride. Enzymes include, but are not limited to, lysozymes, mutanolysin, labiase, lysostaphin, lyticase, proteinase K, endolysin or achromopeptidases. Extraction solvents include, but are not limited to, polyvinylpolypyrrolidone, phenol, trichlorotrifluoroethane or a mixture of phenol and guanidinium thiocyanate or guanidinium chloride. Lysing buffers include, but are not limited to, ammonium chloride, quaternary ammonium compounds, hexadecyltrimethylammonium bromide, cetyltrimethylammonium bromide, sodium dodecyl sulfate, hexametaphosphate, sodium pyrophosphate, Zap-o-globin™, a lysing buffer available commercially from Coulter Diagnostics or CyQUANT™ cell lysis buffer, available commercially from Molecular Probes.

The reagent may be added in any amount suitable for lysing the microbiological matter and may be added in excess. In one embodiment, the reagent is added in an amount of from about 1 mg to about 10,000 mg per liter of aqueous medium. In another embodiment, the reagent is added in an amount of from about 1 mg to about 1000 mg per liter of aqueous medium. In another embodiment, the reagent is added in an amount of from about 1 mg to about 50 mg per liter of aqueous medium.

Physical lysing may occur thermally or by freeze-thawing. Cell lysing can be accomplished thermally by heating the aqueous medium, such as with a thermal block or hot plate. In one embodiment, the aqueous medium is heated to a temperature from about 40° C. to about 100° C. In another embodiment, the temperature is from about 40° C. to about 60° C. In one embodiment, the aqueous medium is heated from about 1 minute to about 1 hour. In another embodiment, the aqueous medium is heated from about 1 minute to about 30 minutes, including from about 1 minute to about 15 minutes. In another embodiment, the aqueous medium is heated from about 1 minute to about 3 minutes.

In one example of freeze-thawing, the aqueous medium is frozen, such as in an ethanol-dry ice bath, and then thawed.

Cells may be lysed electrically with a series of electrical pulses, by diffusive mixing and dielectrophoretic trapping or by microwave radiation. Free radicals may also be used for cell lysing. The method includes applying an electric field to a mixture of a metal ion, peroxide and the microbiological matter in the aqueous medium to generate free radicals, which attack the cell barriers.

The fluorescent signals of the aqueous medium are measured before and after the intracellular content of the microbiological matter has been extracted and released into the aqueous medium to provide a baseline fluorescent signal and a second fluorescent signal, respectively. These fluorescent signals may be recorded manually or may be measured and stored in an online monitoring instrument.

The baseline fluorescent signal is subtracted from the second fluorescent signal to obtain a net fluorescent signal.

The net fluorescent signal may be equated with a total microbiological content. A calibration curve may be prepared for a selected fluorescent dye from known concentrations of microbiological matter and fluorescence measurements of the concentration. In one embodiment, the concentrations of microbiological matter are determined by plate count method. In one embodiment, several samples containing known total microbiological contents and the selected fluorescent dye are measured to obtain fluorescent signals. The log numbers of these signals are plotted on a graph and regression analysis may be performed to obtain a calibration curve equating total microbiological content with fluorescent signals.

Total bacterial concentration can be measured quickly and depending on the method selected for releasing extracellular contents of the biological matter, assays can be completed within 5 minutes. The rapid assays are well-suited to laboratory use, field applications, on-line automated batch systems or off-line monitoring systems. In another embodiment, the assays may be automated and performed continuously.

In another embodiment, a background fluorescent signal may be obtained to remove background interference and improve the accuracy of measuring the microbiological content in an aqueous medium. A background signal may be obtained by measuring the fluorescence of any additional organic or non-cellular components. In one embodiment, a background signal is subtracted from the net fluorescent signal. In one embodiment, a process for measuring total microbiological content in an aqueous medium includes adding a fluorescent dye to an aqueous medium portion, obtaining an additional aqueous medium portion for a background aqueous medium portion, treating the background aqueous medium portion to remove microbiological matter, adding a fluorescent dye to the treated background aqueous medium portion, measuring a fluorescent signal in the aqueous medium portion to obtain a baseline fluorescent signal, measuring a fluorescent signal in the treated background aqueous medium portion to obtain a background baseline fluorescent signal, releasing intracellular content of the microbiological matter in the aqueous medium portion into the aqueous medium by lysing the microbiological matter, simulating the lysing procedure in the background aqueous medium portion, measuring the fluorescent signal in the aqueous medium portion with the released microbiological intracellular content to obtain a second fluorescent signal, measuring the fluorescent signal in the simulated background aqueous medium portion to obtain a second background fluorescent signal, subtracting the baseline signal from the second fluorescent signal to obtain a net fluorescent signal, subtracting the background baseline fluorescent signal from the second background fluorescent signal to obtain a net background signal, adjusting the net fluorescent signal with the net background signal and equating the adjusted net fluorescent signal with a microbiological content.

The aqueous media is described above. Background signals may be obtained for any type of aqueous media, but are most helpful for aqueous media with high amounts of organics or non-cellular components that fluoresce in the presence of the fluorescent dye, such as process water from crude oil processing. In one embodiment, the aqueous medium portion and the background aqueous medium portion have the same volume.

Adding the fluorescent dye and steps for obtaining the baseline fluorescent signal, releasing the intracellular content of the microbiological matter, obtaining a second fluorescent signal and obtaining a net fluorescent signal are described above.

The aqueous medium may be treated to remove the microbiological matter. The microbiological matter may be removed from the aqueous medium for obtaining a background signal by heating the aqueous medium or by treating the aqueous medium with biocides, such as bleach, chlorine, other commercial biocides or combinations thereof. In one embodiment, chlorine is used in an amount of from about 0.1 ppm to about 30 ppm. In another embodiment, chlorine is used in an amount of from about 0.1 ppm to about 20 ppm, including from about 0.1 ppm to about 10 ppm. The biocide may be used in an amount of from about 1 ppm to about 200 ppm. In another embodiment, the biocide is used in an amount of from about 1 ppm to about 100 ppm, including from about 1 ppm to about 50 ppm. When using chlorine, it may be necessary to neutralize the chlorine after the background microbiological effect is minimized. In one embodiment, sodium meta bisulfite is used to neutralize the chlorine. In one embodiment, sodium meta bisulfite is added to the aqueous medium in an amount of from about 1 ppm to about 500 ppm. In another embodiment, sodium meta bisulfite is added to the aqueous medium in an amount of from about 1 ppm to about 300 ppm, including from about 1 ppm to about 200 ppm.

In another embodiment, the microbiological matter components may be removed by heating the aqueous medium, such as with a thermal block or hot plate. In one embodiment, the aqueous medium is heated to a temperature from about 40° C. to about 100° C. In another embodiment, the temperature is from about 40° C. to about 70° C. In another embodiment, the temperature is from about 40° C. to about 60° C. In one embodiment, the aqueous medium is heated from about 1 minute to about 1 hour. In another embodiment, the aqueous medium is heated from about 1 minute to about 30 minutes, including from about 1 minute to about 15 minutes. In another embodiment, the aqueous medium is heated from about 1 minute to about 3 minutes.

A background baseline fluorescent signal may be obtained by measuring the fluorescence of the aqueous medium portion that was treated to remove microbiological matter. The excitation and emission wavelengths depend on the fluorescent dye selected. In one embodiment, the excitation wavelength is from about 350 nm to about 600 nm and the emission wavelength is from about 450 nm to about 650 nm. Fluorescence may be measured by a fluorescence detector as described above. The background baseline signal can be recorded manually or is measured and stored in an online monitoring instrument.

The lysis procedure may be simulated in the treated background aqueous medium portion. In one embodiment, the process for releasing intracellular microbiological content into the aqueous medium portion is repeated in the background aqueous medium portion in which the microbiological matter has been removed. Lysing may be performed using mechanical, chemical, physical, electrical, ultrasonic or microwave methods or any combination of these methods, as is described above.

A second background fluorescent signal may be obtained by measuring the fluorescence of the simulated background aqueous medium. The excitation and emission wavelengths depend on the fluorescent dye selected. In one embodiment, the excitation wavelength is from about 350 nm to about 600 nm and the emission wavelength is from about 450 nm to about 650 nm. Fluorescence may be measured by a fluorescence detector, which are described above. The second background fluorescent signal can be recorded manually or is measured and stored in an online monitoring instrument.

The background baseline fluorescent signal may be subtracted from the second background fluorescent signal to obtain a net background signal. The net fluorescent signal may be adjusted by subtracting the net background signal from the net fluorescent signal to obtain an adjusted net fluorescent signal.

The adjusted net fluorescent signal may be equated with a total microbiological content. A calibration curve may be prepared for a selected fluorescent dye from known concentrations of microbiological matter and fluorescence measurements. In one embodiment, several samples containing known total microbiological contents and the selected fluorescent dye are measured to obtain fluorescent signals. The log numbers of these signals are plotted on a graph and regression analysis is performed to obtain a calibration curve equating total microbiological content with fluorescent signals.

Portions of the aqueous medium may be removed manually or may be removed systematically by an online testing device.

In another embodiment, the concentration of biofilm may be quantified. Biofilms cling to surfaces, including, but not limited to, glass, plastic, metal or paint, and can be dislodged from the surfaces and dispersed in an aqueous medium to measure the total microbiological content of the biofilm. In one embodiment, a process for measuring biofilm content in an aqueous medium includes dispersing biofilm into the aqueous medium, adding a fluorescent dye to the aqueous medium, measuring the fluorescent signal in the aqueous medium to obtain a baseline fluorescent signal, releasing intracellular content of the microbiological matter into the aqueous medium by lysing the microbiological matter, measuring the fluorescent signal in the aqueous medium with the released intracellular content of the microbiological matter to obtain a second fluorescent signal, subtracting the baseline fluorescent signal from the second fluorescent signal to obtain a net fluorescent signal and equating the net fluorescent signal with a microbiological content.

Biofilms or sessile microbes must be detached from surfaces and dispersed in an aqueous media to quantify the microbial concentration of the biofilms. Aqueous medium may be any type of aqueous media into which biofilm microbes have been dislodged or dispersed. In one embodiment, the biofilms are dispersed in a saline solution. In another embodiment, the biofilms are dispersed in a buffered saline solution. In another embodiment, the aqueous media may be a phosphate buffer solution. In another embodiment, the aqueous medium is water. In another embodiment, the water may be municipal water or industrial water, such as cooling tower water.

The microbial cells may be peeled or dislodged from the growth surface and dispersed into the aqueous medium by any suitable manner that does not disrupt the individual cell structure and may be achieved through a physical method, a mechanical method, a chemical method or a combination of these methods. Examples of physical methods for detaching and dispersing biofilm cells include, but are not limited to, agitation, vortexing, shaking and washing with strong shear stress. In one embodiment, the biofilm is dispersed with vortexing. In one embodiment, a biofilm coupon is submerged in a liquid and the cells are dislodged from the coupon by creating a flow of fluid that vortexes or swirls rapidly around as in a cyclone for a suitable time to release the cells from the aggregate. In one embodiment, the biofilm is vortexed for about 5 seconds to about 5 minutes. In another embodiment, the biofilm is vortexed from about 10 seconds to about 3 minutes. In another embodiment, the biofilm is vortexed from about 15 seconds to about 1 minute. In another embodiment, the biofilm is vortexed for about thirty seconds.

Examples of mechanical methods for detaching and dispersing biofilm cells include, but are not limited to, the use of a sonication bath or an electric current.

Examples of chemical methods for detaching and dispersing biofilm cells include, but are not limited to, adding a surfactant, dispersant or digestive enzyme. Examples of surfactants include, but are not limited to, ethylene oxide and/or propylene oxide (EO/PO) copolymers, dimethylamide polymer, Ultra-Kleen™ biocide, which is commercially available from Sterilex (Owings Mills, Md.), sodium octane sulfonate or alkyl polyglycoside. Examples of enzymes include, but are not limited to, blends of cellulase, alpha-amylase and protease. In one embodiment, the dispersant may be polyethyleneimine After the biofilm has been dislodged and dispersed in the aqueous medium, a total microbial assay is performed. The steps for adding a fluorescent dye to the aqueous medium, measuring the fluorescent signal in the aqueous medium to obtain a baseline fluorescent signal, releasing intracellular content of the microbiological matter into the aqueous medium, measuring the fluorescent signal in the aqueous medium with the released intracellular content of the microbiological matter to obtain a second fluorescent signal, obtaining a net fluorescent signal and equating the net fluorescent signal with a microbiological content are described above.

In another embodiment, the total amount of microbiology (cfu) may be obtained by multiplying the concentration with the known volume of aqueous media into which the biofilm was dislodged. In another embodiment, the amount of microbiology per surface unit area (cfu/cm$^2$) may be obtained by dividing the amount of microbiology by the unit area of surface to which the biofilm was attached.

Biofilm can be measured directly by sampling biofilm from select system surfaces of known dimension. Alternatively, a coupon can be used to grow and measure the propensity of a system to grow biofilm. Some areas of water systems are inaccessible for practical sampling, and coupon testing provides a measure of the propensity for the system to grow biofilm. This method can also provide evidence that a treatment program has successfully reduced the propensity for the treated system to grow biofilm.

In another embodiment, a background fluorescent signal may be obtained to remove background interference and improve the accuracy of measuring the biofilm content in an aqueous medium.

In order that those skilled in the art will be better able to practice the present disclosure, the following examples are given by way of illustration and not by way of limitation.

EXAMPLES

Example 1

Calibration Curve in Phosphate Buffer Saline (PBS)

*Pseudomonas fluorescens* cells were grown over night in a liquid culture media and added to 10 ml of PBS to form an initial sample. Serial dilutions were prepared from the initial sample. 0.1 ml of the initial sample was added to 9.9 ml of PBS to make a 1% ($10^{-2}$) solution. 1 ml of the 1% solution was added to 9 ml of PBS to make a 0.1% ($10^{-3}$) solution. 1 ml of the 0.1% solution was added to 9 ml of PBS to make a 0.01% ($10^{-4}$) solution. 1 ml of the 0.01% solution was added to 9 ml of PBS to make a 0.001% ($10^{-5}$) solution. 10 ml of the PBS was used for a cell-free blank 170 µl samples were taken from each of the diluted samples and the cell-free blank and each sample was mixed with 20 µl of 10×SYBR® Green I dye and 10 µl of 20× CyQUANT™ cell lysis buffer (available commercially from Molecular Probes). Fluorescence intensity was measured for each of the samples (cell-free blank, $10^{-2}$, $10^{-3}$, $10^{-4}$ and $10^{-5}$) at an excitation wavelength of 497 nm and an emission wavelength of 520 nm by an LS55 Luminescence Spectrometer (PerkinElmer). The fluorescence was measured four times for each sample and averaged to obtain a Fluorescence Intensity I signal.

The samples were heated at 60° Celsius for 2 minutes and then cooled down to room temperature. Fluorescence intensity was measured for each of the diluted samples ($10^{-2}$, $10^{-3}$, $10^{-4}$ and $10^{-5}$) at an excitation wavelength of 497 nm and an emission wavelength of 520 nm. The fluorescence was measured four times for each sample and averaged to obtain a Fluorescence Intensity II signal.

A delta fluorescence intensity (Δ) was obtained by subtracting the Fluorescence Intensity I signal from the Fluorescence Intensity II signal.

Concentrations of the total *Pseudomonas fluorescens* bacteria were obtained for each sample (cell-free blank, $10^{-2}$, $10^{-3}$, $10^{-4}$ and $10^{-5}$) using a standard plate count method.

Regression analysis was performed between the log value of the delta fluorescence intensity (relative light unit (RLU)) and the log value of the plate count (cfu/ml) to obtain a calibration curve as shown in FIG. 1. The regression equation is y=−1.37+0.855×(R-Sq=97.6%).

Example 2

Calibration Curve

A calibration curve was prepared as in Example 1 except that filtered water from a cooling tower was used instead of the PBS.

About 50 ml of water from a cooling tower was filtered through a PVDF filter (Millipore SLGV033RB) to remove residual microorganisms. 10 ml of the filtered water was used for a cell-free blank.

Concentrations of the total *Pseudomonas fluorescens* bacteria were obtained for each sample (cell-free blank, $10^{-2}$, $10^{-3}$, $10^4$ and $10^{-5}$) by the plate count method.

Figure 2:
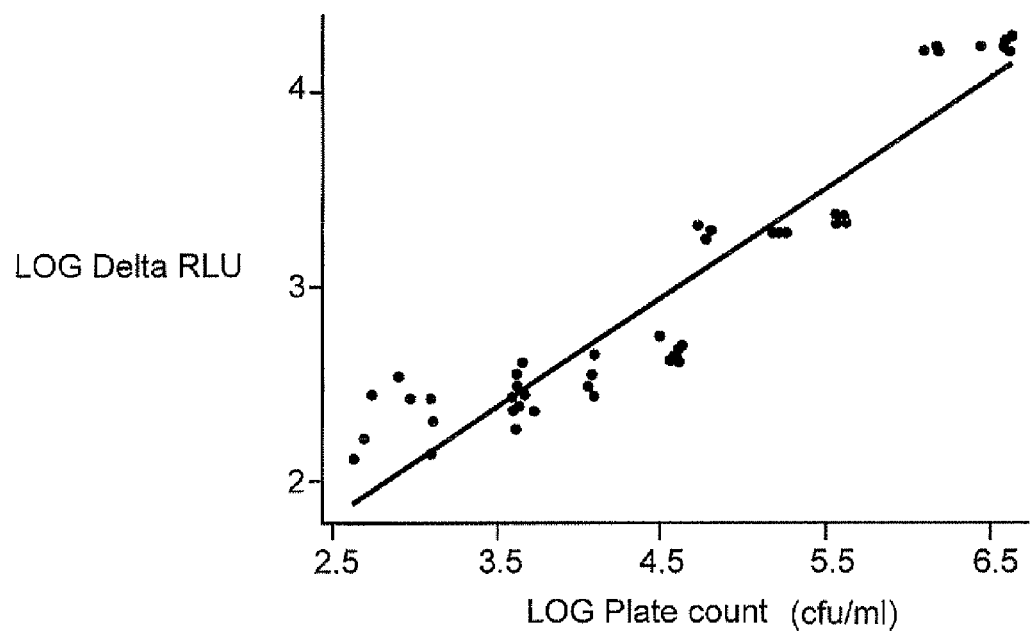
FIG. 2 depicts a graph of a regression plot of LOG delta RLU versus cell concentration (cfu/ml) for *Pseudomonas fluorescens* diluted in filtered cooling tower water.

Regression analysis was performed between the log value of the delta fluorescence intensity (RLU) and the log value of the plate count (cfu/ml) to obtain a calibration curve as shown in FIG. 2. The regression equation is $y=0.383+0.576x$ (R-Sq=90.7%).

Example 3

*Pseudomonas fluorescens* cells were grown over night on a culture plate and added to several 170 μl samples of phosphate buffer saline. Each sample was mixed with 20 μl of 10×SYBR® Green I dye (from Molecular Probes) and 10 μl of 20× CyQUANT™ cell lysis buffer.

Fluorescence intensity was measured for each of the samples at an excitation wavelength of 497 nm and an emission wavelength of 520 nm. The fluorescence was measured four times for each sample and averaged to obtain a fluorescent baseline signal.

The samples were heated at 60° Celsius for 2 minutes and then cooled down to room temperature. Fluorescence intensity was measured for each of the samples at an excitation wavelength of 497 nm and an emission wavelength of 520 nm. The fluorescence was measured four times for each sample and averaged to obtain a second fluorescent signal.

Figure 3:
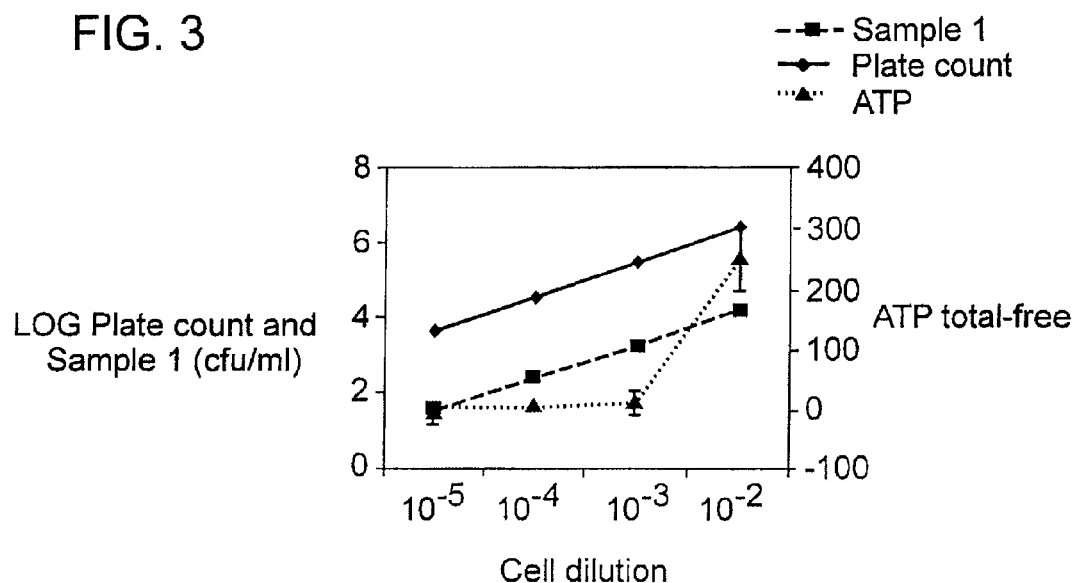
FIG. 3 depicts a graph of assay readings for cell concentration (cfu/ml) based on total microbiological content and plate count and ATP bioluminescence versus cell dilutions for *Pseudomonas fluorescens* diluted in autoclaved phosphate buffer saline (PBS).

A delta fluorescence intensity (Δ) was obtained by subtracting the fluorescent baseline signal from the second fluorescent signal. The log value of the delta fluorescence intensity measurements were equated with a cell concentration (cfu/ml) from the calibration curve prepared in Example 1 and are shown as Sample 1 in FIG. 3. FIG. 3 depicts a graph of assay readings for cell concentration (cfu/ml) and ATP bioluminescence versus cell dilutions for *Pseudomonas fluorescens* diluted in phosphate buffer saline (PBS).

Comparative tests were also prepared on each sample by plate count and Bioscan™ ATP. Four measurements were prepared for each test and averaged and are shown in FIG. 3. Plate Count and the Sample 1 results are reported in log concentrations and ATP results are reported in original concentrations. ATP results had 1-log variance for the same standard and the results were too noisy to be used for quantitative comparisons.

Sample 1 was performed in 5 minutes or less and can measure concentrations as low as $10^4$ cfu/ml with good accuracy. It has a similar variation (standard deviation/mean) and good correlation with traditional culture-based methods, and has much better detection limit and smaller variation compared to the industrial Bioscan™ ATP method.

Example 4

*Pseudomonas fluorescens* cells were grown over night on a culture plate and added to several 170 μl samples of field water that was autoclaved to remove residual microorganisms.

Each sample was mixed with 20 μl of 10×SYBR® Green I dye (from Molecular Probes) and 10 μl of 20× CyQUANT™ cell lysis buffer.

Fluorescence intensity was measured for each of the samples at an excitation wavelength of 497 nm and an emission wavelength of 520 nm. The fluorescence was measured four times for each sample and averaged to obtain a fluorescent baseline signal.

The samples were heated at 60° Celsius for 2 minutes and then cooled down to room temperature. Fluorescence intensity was measured for each of the samples at an excitation wavelength of 497 nm and an emission wavelength of 520 nm. The fluorescence was measured four times for each sample and averaged to obtain a second fluorescent signal.

Figure 4:
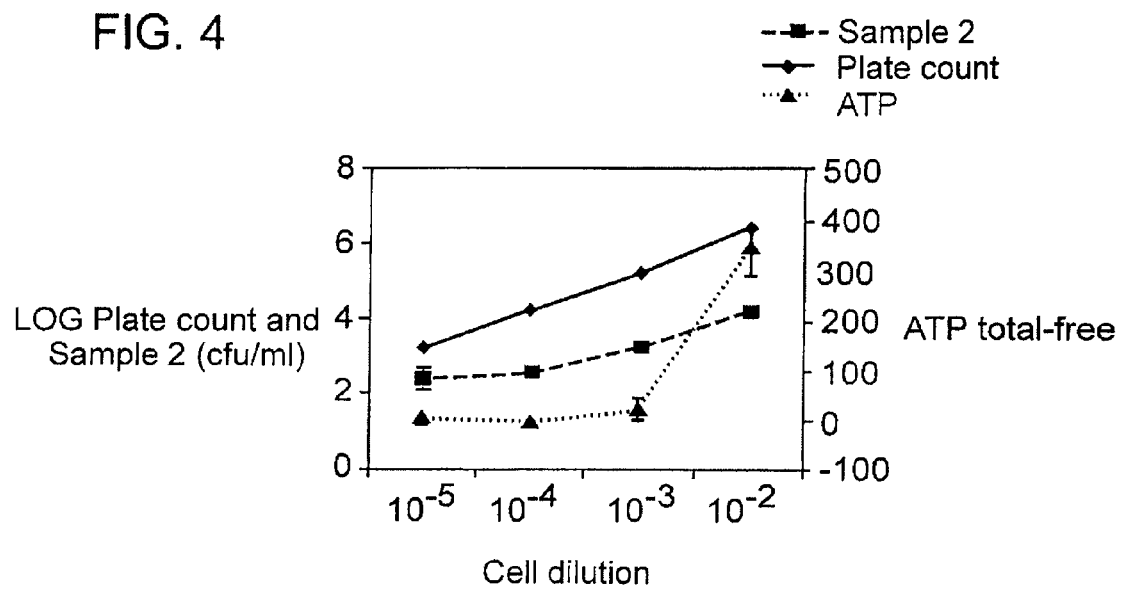
FIG. 4 depicts a graph of assay readings for cell concentration (cfu/ml) based on total bacterial assay and plate count and ATP bioluminescence versus cell dilutions for *Pseudomonas fluorescens* diluted in filtered cooling tower water.

A delta fluorescence intensity (Δ) was obtained by subtracting the fluorescent baseline signal from the second fluorescent signal. The log values of the delta fluorescence intensity measurements were equated with a cell concentration (cfu/ml) from the calibration curve prepared in Example 2 and are shown as Sample 2 in FIG. 4. FIG. 4 depicts a graph of assay readings for cell concentration (cfu/ml) and ATP bioluminescence versus cell dilutions for *Pseudomonas fluorescens* diluted in field water.

Comparative tests were also prepared on each sample by plate count and Bioscan™ ATP. Four measurements were prepared for each test and averaged and are shown in FIG. 4. Plate Count and the Sample 2 results are reported in log concentrations and ATP results are reported in original concentrations. The ATP results had 1-log variance for the same standard and the results were too noisy to be used for quantitative comparisons.

Sample 2 was performed in 5 minutes or less and can measure concentrations as low as $10^4$ cfu/ml with good accuracy. It has a similar variation (standard deviation/mean) and good correlation with traditional culture-based methods, and has much better detection limit and smaller variation compared to the industrial Bioscan™ ATP method.

Example 5

Calibration curves were prepared for *Pseudomonas fluorescens* bacteria in cooling tower water and in phosphate buffer saline (PBS). About 50 ml water from a cooling tower was autoclaved to remove residual microorganisms.

*Pseudomonas fluorescens* cells were grown over night in a liquid culture media and added to 10 ml of the autoclaved cooling tower water to form an initial sample. Serial dilutions were prepared from the initial sample. 0.1 ml of the initial sample was added to 9.9 ml of autoclaved cooling tower water to make a 1% ($10^{-2}$) solution. 1 ml of the 1% solution was added to 9 ml of autoclaved cooling water to make a 0.1% ($10^{-3}$) solution. 1 ml of the 0.1% solution was added to 9 ml of autoclaved cooling water to make a 0.01% ($10^{-4}$) solution. 1 ml of the 0.01% solution was added to 9 ml of autoclaved cooling tower water to make a 0.001% ($10^{-5}$) solution. 10 ml of the autoclaved cooling tower water was used for a blank.

*Pseudomonas fluorescens* cells were added to 10 ml of the PBS to form an initial sample. Serial dilutions were prepared from the initial sample as for the cooling tower water to make PBS solutions of $10^{-2}$, $10^{-3}$, $10^{-4}$ and $10^{-5}$. 10 ml of the PBS was used for a blank A sample from each water and PBS serial dilution was set aside for measuring background noise in the water samples. Each background sample was treated with a biocide composed of 1 ppm chlorine and 20 ppm Bellacide® 350 for 30 minutes. 200 ppm sodium bisulfite was added to neutralize the residual chlorine.

170 μl samples were taken from each of the diluted cooling tower water PBS samples and background samples. Each sample was mixed with 20 μl of 10×SYBR® Green I dye (from Molecular Probes) and 10 μl of 20× CyQUANT™ cell lysis buffer.

Fluorescence intensity was measured for each of the cooling tower water and PBS samples at an excitation wavelength of 497 nm and an emission wavelength of 520 nm. The fluorescence was measured four times for each sample and averaged to obtain a Fluorescent I signal. Fluorescence intensity was measured for each of the background cooling tower water samples at an excitation wavelength of 497 nm and an emission wavelength of 520 nm. The fluorescence was measured four times for each sample and averaged to obtain a Background Fluorescent I signal.

The samples were heated at 60° Celsius for 2 minutes and then cooled down to room temperature. Fluorescence intensity was measured again for each of the cooling tower water and PBS samples at an excitation wavelength of 497 nm and an emission wavelength of 520 nm. The fluorescence was measured four times for each sample and averaged to obtain a Fluorescent II signal. Fluorescence intensity was measured for each of the background cooling tower water samples at an excitation wavelength of 497 nm and an emission wavelength of 520 nm. The fluorescence was measured four times for each sample and averaged to obtain a Background Fluorescent II signal.

A net fluorescence intensity was obtained by subtracting the Fluorescent I signal from the Fluorescent II signal. Net fluorescent measurements were obtained for each cooling tower water and PBS sample.

A net background fluorescent intensity was obtained by subtracting the Background Fluorescent Intensity I signal from the Background Fluorescent Intensity II signal. Net background fluorescent measurements were obtained for each background sample.

Adjusted net fluorescent signals were obtained by subtracting the net background fluorescent signal from the net fluorescent signal for each sample.

Concentrations of the total *Pseudomonas fluorescens* bacteria were obtained for each cooling tower water and PBS sample using a standard plate count method.

Figure 5:
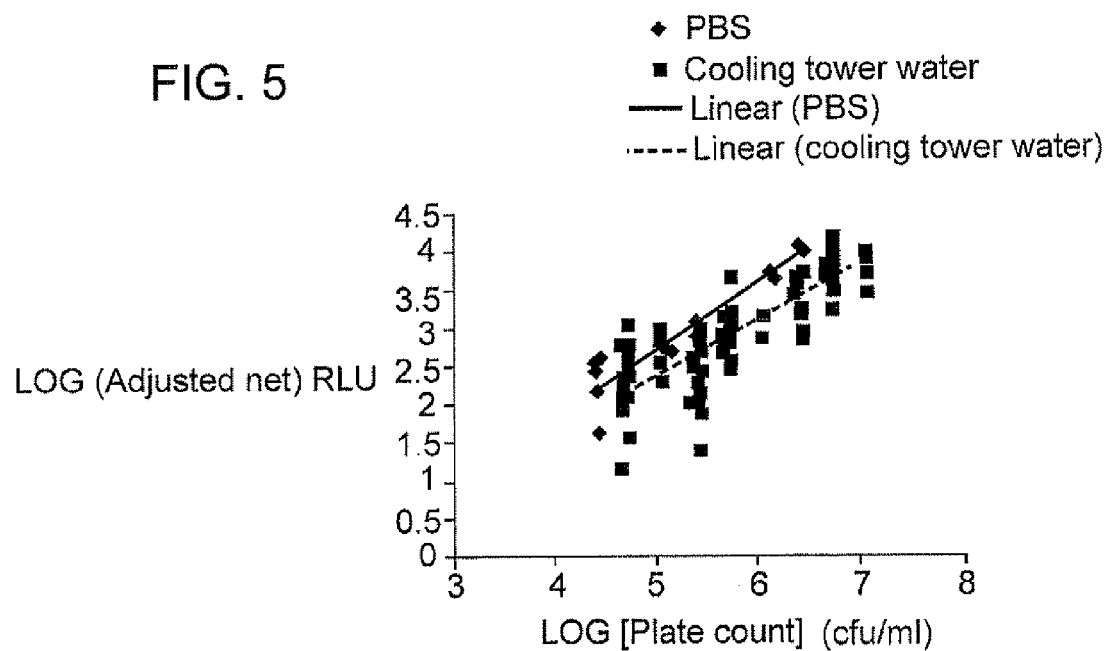
FIG. 5 depicts a graph of a regression plot of LOG delta delta RLU versus LOG cell concentration (cfu/ml) for *Pseudomonas fluorescens* diluted in autoclaved cooling tower water.

Regression analysis was performed between log value of the adjusted net fluorescent signal (RLU) and the log value of the plate count (cfu/ml) to obtain calibration curves for the cooling tower water and the PBS, as shown in FIG. 5. The regression equation for the PBS calibration curve is $y=-1.47+0.847 \times$ (R-Sq=92.2%). The regression equation for the cooling tower water is $y=-1.29+0.741 \times$ (R-Sq=73.7%). Three outliers out of 165 data points were deleted.

Example 6

A calibration curve was prepared as in Example 1 except that the bacteria was *Pseudomonas aeruginosa* cells that were grown over night in a trypic soy broth (TSB) liquid culture media and added to 10 ml of 0.85% saline buffer to form an initial sample.

Serial dilutions were prepared from the initial sample. 0.1 ml of the initial sample was added to 9.9 ml of 0.85% saline buffer to make a 1% ($10^{-2}$) solution. 1 ml of the 1% solution was added to 9 ml of 0.85% saline buffer to make a 0.1% ($10^{-3}$) solution. 1 ml of the 0.1% solution was added to 9 ml of 0.85% saline buffer to make a 0.01% ($10^{-4}$) solution. 1 ml of the 0.01% solution was added to 9 ml of 0.85% saline buffer to make a 0.001% ($10^{-5}$) solution. 10 ml of the 0.85% saline buffer was used for a cell-free blank 180 μl were taken from each of the diluted samples and the cell-free blank and each sample was mixed with 20 μl of 10×SYBR® Green I dye. Fluorescence intensity was measured for each of the samples (cell-free blank, $10^{-2}$, $10^{-3}$, $10^{-4}$ and $10^{-5}$) at an excitation wavelength of 497 nm and an emission wavelength of 520 nm by an LS55 Luminescence Spectrometer (PerkinElmer). The fluorescence was measured four times for each sample and averaged to obtain a baseline fluorescent measure.

The samples were heated to 90° C. for 2 minutes and then cooled to room temperature. Fluorescence intensity was measured at an excitation wavelength of 497 nm and an emission wavelength of 520 nm to obtain a fluorescent intensity II measurement. The fluorescence was measured four times for each sample and averaged to obtain a Fluorescent intensity II measurement.

A delta fluorescence intensity was calculated by subtracting the baseline fluorescent signal from the Fluorescent intensity II signal.

Concentrations of the total *Pseudomonas aeruginosa* cells were obtained for each sample (cell-free blank, $10^{-2}$, $10^{-3}$, $10^{-4}$ and $10^{-5}$) using a standard plate count method.

Figure 6:
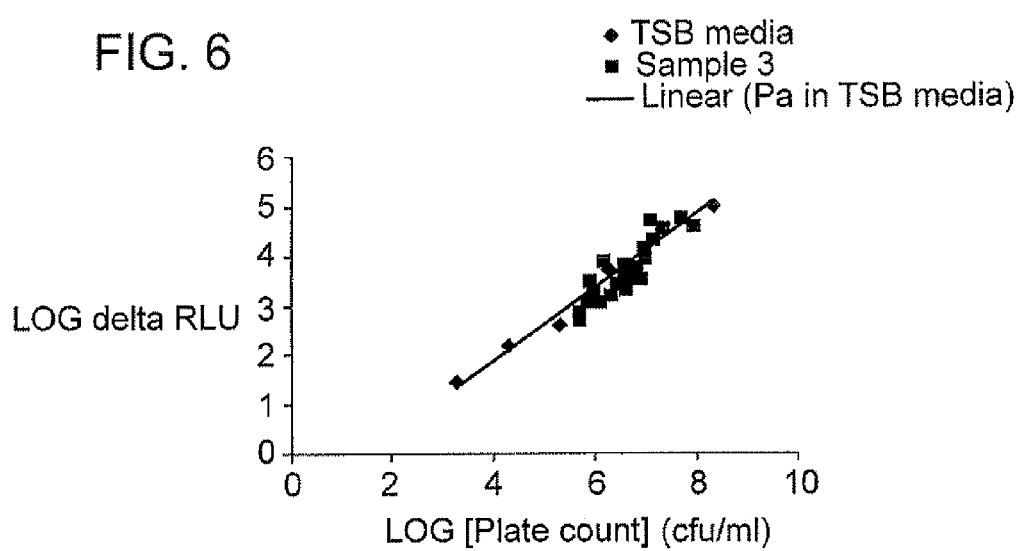
FIG. 6 depicts a graph of a regression plot of LOG delta RLU versus LOG cell concentration (cfu/ml) for *Pseudomonas aeruginosa* biofilm suspended in 0.85% saline buffer.

Regression analysis was performed between the log value of the delta fluorescence intensity (RLU) and the log value of the plate count (cfu/ml) to obtain a calibration curve as shown in FIG. 6. The regression equation is $y=-1.0185+0.7381 \times$ (R-Sq=98.97%).

*Pseudomonas aeruginosa* biofilm cells were grown over night on a 316 stainless steel tubing inner surface by providing a recycling flow of liquid growth media, 30% TSB media with 1% bacteria inoculum (over-night culture) through the tubing in a recycling circuit with a 135 ml/min flow rate.

A segment of the 316 stainless steel tube was removed from the flow system after a desired time interval. The biofilm build-up was dislodged by immersing the 316 stainless steel tube segment in 10 ml of 0.85% saline buffer and vortexed for 2 minutes at maximum speed.

Several aliquots of 180 μl of the vortexed sample were mixed with 20 μl of 10×SYBR® Green I dye. Fluorescence intensity was measured for each sample at an excitation wavelength of 497 nm and an emission wavelength of 520 nm. The fluorescence was measured four times for each sample and averaged to obtain a baseline fluorescent measurement.

The samples were heated to 90° C. for 2 minutes and then cooled to room temperature. Fluorescence intensity was measured for each of the samples at an excitation wavelength of 497 nm and an emission wavelength of 520 nm. The fluorescence was measured four times for each sample and averaged to obtain a fluorescent intensity II measurement.

A delta fluorescence intensity was calculated by subtracting the fluorescent baseline signal from the fluorescent intensity II signal. The log value of the delta fluorescent intensity measurements (RLU) were plotted along the calibration curve in FIG. 6 as Sample 3 data points. The log value of the delta fluorescent intensity measurements for each of the samples can be equated with a cell concentration (cfu/ml) from the calibration curve in FIG. 6.

From FIG. 6, it is can be seen that all the data points from the *Pseudomonas aeruginosa* biofilm cells (Sample 3) aligned well with the calibration curve obtained from the planktonic *Pseudomonas aeruginosa* cells suspension, which indicate this assay is suitable for biofilm quantification after dispersing the biofilm from the solid surface.

Figure 7:
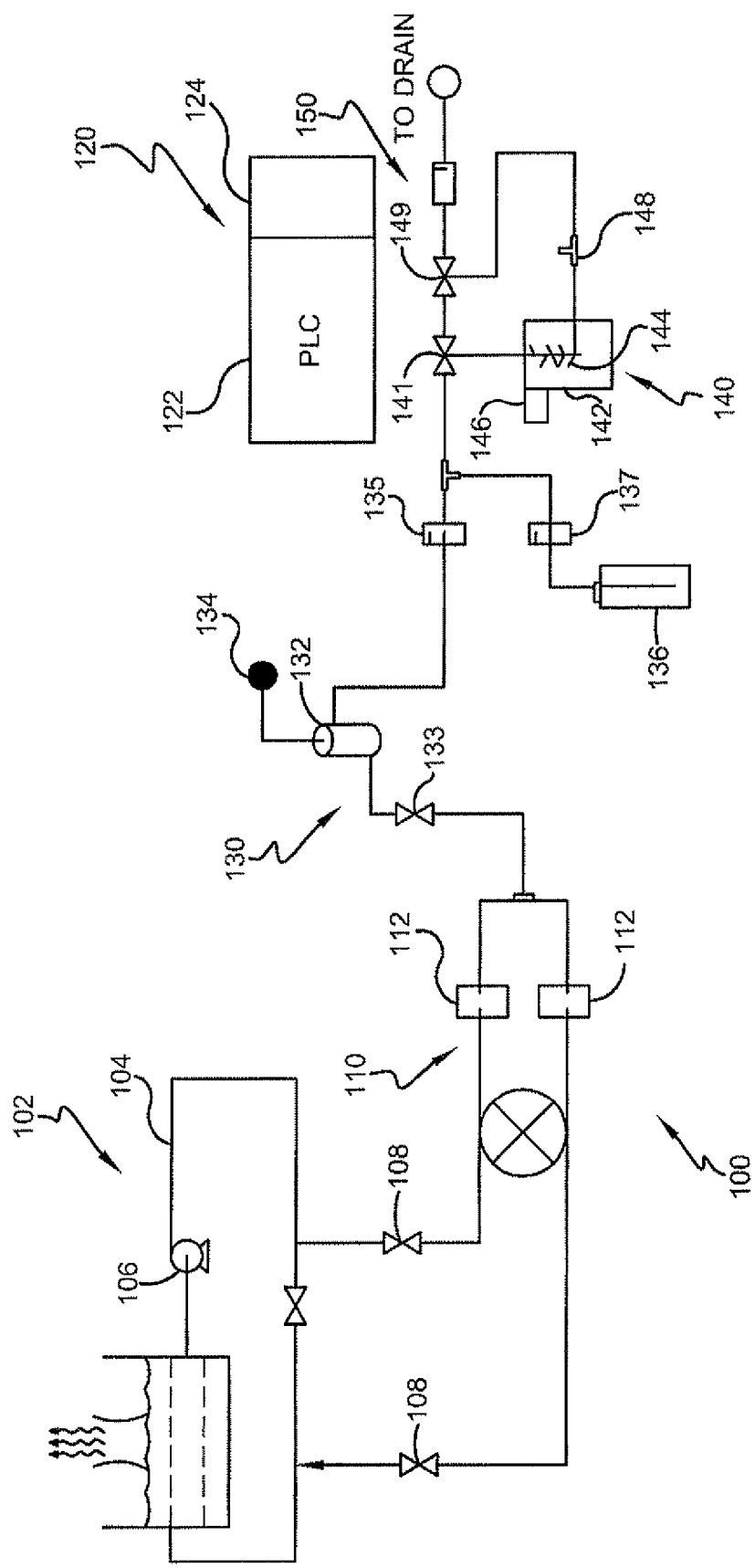
FIG. 7 is a schematic drawing of a system for monitoring the total bacterial content in an aqueous medium according to the invention.

Referring now to FIG. 7, a system for monitoring the total bacterial content in the aqueous medium of a water system according to the methods set forth above is illustrated and referred to generally by reference number 100. The embodiment shown in FIG. 7 illustrates a conventional open recirculating cooling tower water system 102 having an aqueous medium flowing through a circulating loop 104. Flow of the aqueous medium through the circulating loop 104 may be assisted by a circulating pump 106 as is known in the art.

Valves 108 permit feeding aqueous medium from the circulating loop 104 to the total bacterial monitoring system 100. The total bacterial monitoring system 100 works as an on-line analyzer to monitor bacteria concentration in the aqueous medium of the water system 102. One skilled in the art will understand that the total bacterial monitoring system 100 may be used to provide for rapid detection of total viable bacteria through the measurement of total bacteria in any municipal or industrial water or process system 102. Accordingly, further details of the water system 102 need not be given herein.

The aqueous medium entering the total bacterial monitoring system 100 first passes through a filter module 110. Desirably, the filter module 110 includes a filter 112 having a pore size of between about 5 and about 50 microns such that larger impurities are removed from the aqueous medium, but the bacterial content passes through in the filtrate. In one embodiment, the filter module 110 is a flip/flop type filter system such as the one disclosed in commonly assigned U.S. patent application Ser. No. 12/193,198 filed Aug. 18, 2008 entitled "In-Line Filtration Systems", with a filter pore size of 10 microns. However, the filter module 110 may include other filtering layouts without departing from the scope of the invention.

The total bacterial monitoring system 100 includes a control module 120, a sample preparation module 130, a cell lysing module 140, and a detection module 150. The control module 120 contains a programmable logic controller 122 or similar device and an electronics unit 124 used to control the function of the other modules 130, 140, 150, and additionally calculates the total bacteria concentration as will be described below.

The sample preparation module 130 is comprised of a level-switch sample cup 132 and a solenoid valve 133 used to control the flow of the filtered aqueous medium into the sample cup 132. In one embodiment, the level-switch sample cup 132 is comprised of a pair of lead wires. When the sample cup 132 is full, or at a designated high level, the two wires are electronically connected, which triggers the shutoff of the solenoid valve 133. When the sample cup 132 is empty, or at a designated low level, the two wires are disconnected, which triggers the opening of the solenoid valve 133. The dead band between these two states is desirably about 1.5 ml. The sample preparation module 130 lets down the pressure of the aqueous medium from header pressure in the circulating loop 104 to atmospheric pressure. Desirably, the sample cup 132 is open to the atmosphere so as to allow any air bubbles in the aqueous medium to escape from the sample through vent 134. As one skilled in the art would understand, air bubbles in the aqueous medium would cause unwanted spikes from optical measurement devices used in the detection module 150.

A sample pump 135, such as a micro positive-displacement pump, draws aqueous medium from the sample cup 132. By lowering the pressure, the sample pump 135 is protected, as the sample pump may be rated for only about 5 psig. The feed rate of the aqueous medium through the sample preparation module 130 is controlled using the sample pump 135. The programmable logic controller 122 sets the stroke frequency of the sample pump 135 to accurately control the flow rate. Flow rates of the aqueous medium are desirably between about 100 uL and about 250 uL, and more desirably between about 150 uL and about 200 uL. In one embodiment, the sample pump 137 is a model 150SP-S2 made by Beion Medical Technology Co. However, any known pump capable of accurately pumping small volumes of aqueous medium may be used.

In the illustrated embodiment, the fluorochrome reagent and the buffer are premixed and added together to the aqueous medium from a reagent supply 136. Alternately, one skilled in the art will understand that the buffer may be added before or after the fluorochrome is added to the aqueous medium. The reagent supply 136 feeds the fluorochrome and buffer by means of a reagent feed pump 137. The reagent feed pump 137 also is desirably a micro positive-displacement pump and the programmable logic controller 122 sets its stroke frequency to accurately control the flow rate. Desirably, the reagent feed pump 137 adds the fluorochrome in an amount of from about 0.5 mg to about 100 mg fluorochrome per liter of aqueous medium. The buffer is added to the aqueous medium to maintain the pH of the aqueous medium from about 2 to about 10. In one embodiment, the reagent pump is a model 120SP-S2 made by Beion Medical Technology Co.

The aqueous medium pumped by the sample pump 135 and the reagent pumped by the reagent feed pump 137 are combined using a mixing tee 138, broadly a mixing device, that provides a turbulent flow path to encourage mixing of the aqueous medium and the fluorochrome reagent and buffer. Other mixing devices, such as mixing crosses or impellers, may also be used without departing from the scope of the invention.

In the illustrated embodiment, the lysing module 140 accomplishes cell lysing by heating the aqueous medium. Aqueous medium the sample preparation module 130 is either directed to the lysing module 140 or directed straight to the detection module 150, thus bypassing the lysing module 140, using a three-way valve 141 controlled by the control module 120. In one embodiment, the lysing module 140 includes a temperature control unit 142 that raises and lowers the temperature of the aqueous medium in order to lyse the cells and release the intracellular content of the microbiological matter. The temperature control module 142 includes a heating device 144, such as a semiconductor plate or other known heating elements, to heat the aqueous medium. A fan or other radiator 146 is used to promote rapid cooling of the sample after the cells have been lysed. A thermocouple 148 measures the temperature of the aqueous medium during the heating and cooling periods. The control module 120 controls and supplies power to the temperature control unit 142 to heat the sample to a desired temperature to lyse the cells, and then cool down the sample until it reaches a desired temperature using a predefined control program. Desirably, the temperature control unit 142 heats the aqueous medium to a temperature of between about 40° C. and about 100° C., and more desirably between about 40° C. and about 60° C. The temperature control unit 142 desirably heats the aqueous medium to the desired temperature in a time from about 1 minute to about 1 hour, and more desirably between about 1 minute and about 3 minutes, in order to lyse the cells. One skilled in the art will understand that the temperature control unit 142 may contain other known means to heat and cool the aqueous medium as desired. Additionally, as set forth above, the lysing module 140 may use other known lysing methods, such as mechanical, chemical, physical, electrical, ultrasonic or microwave methods, to lyse the cells without departing from the scope of the invention.

Figure 8:
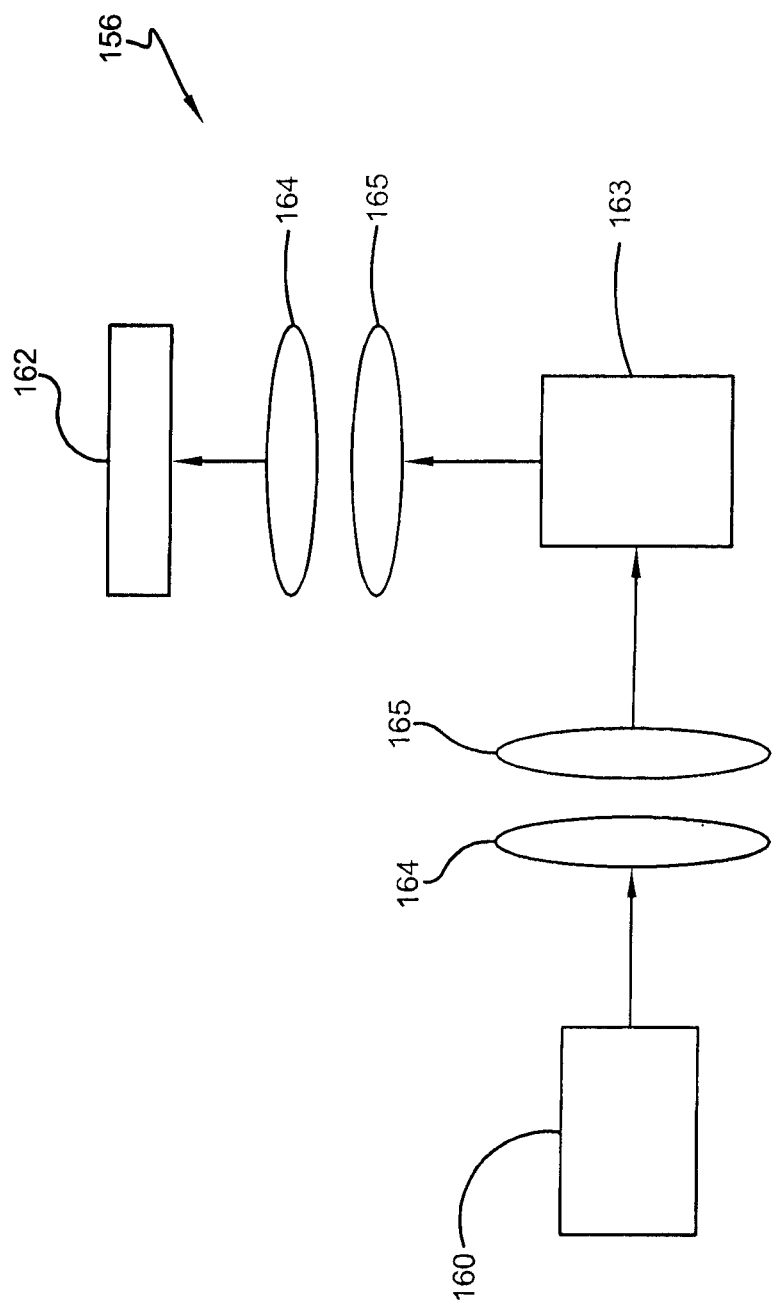
FIG. 8 is an optical measurement unit of the total bacteria monitoring system of FIG. 7.

The aqueous medium containing the lysed biological content is then directed to the detection module 150 through three-way valve 149. The detection module 150 includes an optical measurement unit 152. The use of more than one optical measurement unit may strengthen the accuracy of measurement. The optical measurement unit 152 includes a silicon glass flow cell 154 and a single-wavelength fluorometer 156. The silicon glass flow cell 154 has an inlet flow tube 158 and an outlet flow tube 159 mounted at the bottom and the top of the flow cell, respectively. As best seen in the schematic embodiment illustrated in FIG. 8, the fluorometer 156 includes at least one pair of light-emitting diodes (LEDs) 160 and photodiode emission detectors 162 are configured around a reaction tube 163. Desirably, the fluorescent signal is measured with fluorometer having an excitation wavelength from about 350 nm to about 600 nm and an emission wavelength from about 450 nm to about 650 nm. Additionally, the fluorometer 156 includes optical lenses 164 and filters 165 in the sealed optical tube to control light path and intensity. In one embodiment, the fluorometer 156 is an LS55 Luminescence Spectrometer by PerkinElmer.

In one embodiment comprising three pairs of photo optical components, three LEDs and three photodiodes are installed in six radial channels perpendicular to the center through hole. The three LEDs generate incident light at different wavelengths, and the three corresponding photodiodes detect the respective transmittance on the opposite sides. The LEDs used include a tricolor with 467 nm (blue), 530 nm (green), and 634 nm (red) lights, an orange LED with 610 nm maximum and light green LED with 586 nm maximum emission. This configuration simplifies the design and maintenance of the optical components. The three pairs of photo optical components provide the ability to measure three functions at a time. There is no maximum number of pairs of photo optical components that may be included; however, the number will be affected by size limitations based on the intended use of the monitoring system.

The effluent from the optical measurement unit 152, comprising the mixed sample water and reagents, exits the detector module 150 and connects to a drain or a collection drum, depending on each plant's permitting requirements. Since the effluent is a non-hazardous wastewater, it is commonly discharged to a gravity drain.

The control module 120 is programmed such that fluorescent signals of the aqueous medium are measured by the detection module 150 before and after the intracellular content of the microbiological matter has been extracted and released into the aqueous medium in the lysing module 140 to provide a baseline fluorescent signal and a second fluorescent signal, respectively. These fluorescent signals are measured by the detection module 150 and stored in the programmable logic controller 122. The baseline fluorescent signal is subtracted from the second fluorescent signal to obtain a net fluorescent signal that is a result of the microbiological content of the lysed cells. A calibration curve is used to obtain the total microbiological content as described above. As explained above, the calibration curve is prepared by measuring fluorescent signals for known concentrations of microbiological matter in aqueous media with the fluorochrome, determining the net fluorescent signal for each concentration, plotting the concentration amounts versus log values of the net fluorescent signals on a graph and performing regression analysis to obtain the calibration curve. With above features, the system can monitor total bacteria in an on-line manner While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

What is claimed is:

1. A system for measuring total microbiological content in an aqueous medium flowing through a circulating loop having cellular microbiological components therein and non-cellular organic components therein, comprising:

a filtering module comprising a filter having a pore size between about 5 and about 50 microns for removing impurities from the aqueous medium entering said system;

a sample preparation module configured to add a fluorescent dye to the aqueous medium, wherein said fluorescent dye is an asymmetrical cyanine dye;

a lysing module configured to contact at least a portion of said aqueous medium and to release an intracellular content of said cellular microbiological components into the aqueous medium;

a detection module having an optical measurement unit therein configured to measure a fluorescent signal from said non-cellular organic components in a sample of the aqueous medium to obtain a baseline fluorescent signal, and to measures a fluorescent signal from said non-cellular components and said intracellular content in said portion of the aqueous medium that contacts the lysing module to obtain a second fluorescent signal;

a directing module operatively connected to said circulating loop, to said sample preparation module; to said lysing module; and to said detection module; said directing module configured to direct at least a portion of said aqueous medium to contact said lysing module; and a control module operatively connected to said directing module and to said detection module and configured to subtract the baseline fluorescent signal from the second fluorescent signal to obtain a net fluorescent signal and equate said net fluorescent signal with a microbiological content of the aqueous medium.

2. The system of claim 1 wherein the fluorescent dye is added to the aqueous medium using a reagent addition pump and mixed with a mixing device.

3. The system of claim 1 wherein the detection module comprises a fluorometer comprising at least one pair of light-emitting diodes (LEDs) and photodiode emission detectors configured around a reaction tube having an excitation wavelength from about 350 nm to about 600 nm and an emission wavelength from about 450 nm to about 650 nm.

4. The system of claim 1 wherein the lysing module comprises a temperature control unit that raises the temperature of the aqueous medium.

5. The system of claim 4 wherein the temperature control unit raises the temperature of the aqueous medium to a temperature between about 40° C. and about 100° C. to lyse the cells.

6. The system of claim 1 wherein the control module equates the net fluorescent signal with the microbial concentration using a calibration curve.

7. A system for measuring total microbiological content in an aqueous medium flowing through a circulating loop having cellular microbiological components therein and non-cellular organic components therein, comprising:

a filtering module comprising a filter having a pore size between about 5 and about 50 microns for removing impurities from the aqueous medium entering said system;

a sample preparation module configured to add a fluorescent dye to the aqueous medium, wherein said fluorescent dye is an asymmetrical cyanine dye;

means for measuring a fluorescent signal from said non-cellular organic components in the aqueous medium to obtain a baseline fluorescent signal;

means for releasing intracellular content of the microbiological matter into the aqueous medium by lysing the microbiological matter;

means for measuring a fluorescent signal from said non-cellular components and said intracellular content in the aqueous medium with the lysed microbiological matter to obtain a second fluorescent signal;

means for directing least a portion of said aqueous medium from said circulating loop, to said sample preparation module to said measuring means, and to direct at least a portion of said aqueous medium from said sample preparation module to said releasing means before directing said aqueous medium to said measuring means; and a control module operatively connected to said directing means and to said measuring means and configured to subtract the baseline fluorescent signal from the second fluorescent signal to obtain a net fluorescent signal and equate said net fluorescent signal with a microbiological content of the aqueous medium.

8. The system of claim 7 wherein the fluorescent dye is added to the aqueous medium using a reagent addition pump and mixed with a mixing device.

9. The system of claim 7 wherein the means for measuring the fluorescent signal comprises a fluorometer having at least one pair of light-emitting diodes (LEDs) and photodiode emission detectors configured around a reaction tube having an excitation wavelength from about 350 nm to about 600 nm and an emission wavelength from about 450 nm to about 650 nm.

10. The system of claim 7 wherein the means for lysing the microbiological matter is a temperature control unit that raises the temperature of the aqueous medium.

11. The system of claim 10 wherein the temperature control unit raises the temperature of the aqueous medium to a temperature between about 40° C. and about 100° C. to lyse the cells.

12. The system of claim 7 wherein the control module equates the net fluorescent signal with the microbial concentration using a calibration curve.

13. A system for measuring total microbiological content in an aqueous medium flowing through a circulating loop having cellular microbiological components therein and non-cellular organic components therein, comprising:

a filtering module comprising a filter having a pore size between about 5 and about 50 microns for removing impurities from the aqueous medium entering said system;

a sample preparation module configured to add a fluorescent dye to the aqueous medium, wherein said fluorescent dye is an asymmetrical cyanine dye;

a lysing module having a temperature control unit configured to heat at least a portion of the aqueous medium to a temperature from about 40° C. to about 100° C. to release intracellular content of the microbiological components into the aqueous medium;

a detection module having a fluorometer therein configured to measure a fluorescent signal from said non-cellular organic components in a sample of the aqueous medium to obtain a baseline fluorescent signal and to measure a fluorescent signal from said non-cellular components and said intracellular content in said portion of the aqueous medium that contacts said lysing module to obtain a second fluorescent signal, wherein the fluorometer comprises at least one pair of light-emitting diodes (LEDs) and photodiode emission detectors configured around a reaction tube having an excitation wavelength from about 350 nm to about 600 nm and an emission wavelength from about 450 nm to about 650 nm;

a directing module operatively connected to said circulating loop, to said sample preparation module; to said lysing module; and to said detection module; said directing module configured to direct at least a portion of said aqueous medium to contact said lysing module; and a control module operatively connected to said directing module; to said temperature control unit; and to said detection module and configured to subtract the baseline fluorescent signal from the second fluorescent signal to obtain a net fluorescent signal and equate said net fluorescent signal with a microbiological content of the aqueous medium.

14. The system of claim 1, wherein said fluorescent dye is present in an amount of from about 0.5 mg to about 100 mg fluorescent dye per liter of said aqueous medium.

15. The system of claim 7, wherein said fluorescent dye is present in an amount of from about 0.5 mg to about 100 mg fluorescent dye per liter of said aqueous medium.

16. The system of claim 13, wherein said fluorescent dye is present in an amount of from about 0.5 mg to about 100 mg fluorescent dye per liter of said aqueous medium.

17. The system of claim 1, wherein said total microbiological content is measured at a concentration below about $10^4$ colony forming units per milliliter of said aqueous medium, and wherein said total microbiological content is measured in a period of less than about 5 minutes.

18. The system of claim 7, wherein said total microbiological content is measured at a concentration below about $10^4$ colony forming units per milliliter of said aqueous medium, and wherein said total microbiological content is measured in a period of less than about 5 minutes.

19. The system of claim 13, wherein said total microbiological content is measured at a concentration below about $10^4$ colony forming units per milliliter of said aqueous medium, and wherein said total microbiological content is measured in a period of less than about 5 minutes.

20. The system of claim 1, wherein said circulating loop is part of a cooling tower water system.

21. The system of claim 7, wherein said circulating loop is part of a cooling tower water system.

22. The system of claim 13, wherein said circulating loop is part of a cooling tower water system.

* * * * *